US006613348B1

(12) United States Patent
Jain

(10) Patent No.: US 6,613,348 B1
(45) Date of Patent: Sep. 2, 2003

(54) PROCESS OF CONTROLLING ABSORBENCY IN COLLAGEN FLAKES

(76) Inventor: Manoj K. Jain, 11800 Tech Rd., Suite 240, Silver Spring, MD (US) 20904

( * ) Notice: Subject to any disclaimer, the term of this patent is extended or adjusted under 35 U.S.C. 154(b) by 0 days.

(21) Appl. No.: 09/917,825

(22) Filed: Jul. 31, 2001

(51) Int. Cl.$^7$ .......................... A61F 13/00; A61L 15/00; A01N 25/34
(52) U.S. Cl. ........................ 424/443; 424/444; 424/445; 424/446; 424/447; 424/449; 424/402
(58) Field of Search ................................. 424/443, 444, 424/445, 446, 447

(56) References Cited

U.S. PATENT DOCUMENTS

| | | | | |
|---|---|---|---|---|
| 4,925,924 A | * | 5/1990 | Silver et al. ................. | 530/356 |
| 5,824,015 A | * | 10/1998 | Sawyer ......................... | 606/214 |
| 2002/0172708 A1 | * | 11/2002 | Schoenfeldt et al. ........ | 424/426 |

* cited by examiner

Primary Examiner—Thurman K. Page
Assistant Examiner—Isis Ghali
(74) Attorney, Agent, or Firm—Krieg DeVault Lundy, LLP

(57) ABSTRACT

The present invention provides an improved process for controlling the absorbency and other properties of collagen flakes. The process comprises using freeze-dried collagen material and heating the freeze dried collagen material to a predetermined temperature range between 80 C. and 200 C. for a selected period of time. The collagen flakes will have an improved absorbency, density, porosity, and color. The color of the collagen flakes varies from white to brown. The porosity, absorbency, density and color of the collagen is selectively dependent upon the time and temperature used to heat the collagen flakes. The absorption of the collagen material is selected to be between two to twenty times the weight of the product, and the density of the collagen material is selected to be between 0.1 g/cc to 1.0 g/cc. The collagen flakes are ground into a powder after heating, for use as a wound dressing for medium to high exudative wounds.

24 Claims, No Drawings

PROCESS OF CONTROLLING ABSORBENCY IN COLLAGEN FLAKES

BACKGROUND OF THE INVENTION

1. Field of the Invention

The present invention relates in the field of wound dressings. More specifically, the present invention is directed to a process for controlling the absorbency and other physical properties of collagen flakes, particles, or powders used for medium to highly exudative wounds.

2. Description of Related Art

Older Americans make up the largest group of persons developing chronic wounds such as pressure ulcers. In 1992, the number of persons 65 years or older in the U.S. numbered 32.3 million or 12.7 percent of the population. By 2030, it is estimated the number will approach 70 million, 20 percent of the population (Toth 1995 "Cost-Effective Pressure Ulcer Management in Extended Care," Ostomy/Wound Management Vol. 41 No. 7A August 1995). The wound care market has made much progress in regards to the durability and ability to expedite healing over many traditional products. Many efforts have been made to produce products with the increased durability and absorption capabilities. With the recent developments made in collagen, collagen dressings are preferred because of their superior healing properties.

There is an existing market of powdered wound dressings/fillers for the treatment of medium to highly exudative wounds. Examples of commercially available synthetic surgical powder dressings include those sold under the trade names: COMFEEL ULCUS (Colorplast, Denmark), DUO-DERM (Convatec, UK), HyCURE (SouthWest Technologies Inc., USA), & MEDIFIL (Biocore Medical Technologies, Inc. USA).

Accordingly, a number of attempts have been made to improve the use of collagen flakes in wound healing applications.

U.S. Pat. No. 6,136,341 (Petito) discloses a method and composition used to promote healing wherein the composition is in the form of a powder and has a moisture content of approximately 4 to 7% and a pH range from 5.5 to 6.5. The powder is used on wounds with a large amount of exudate.

U.S. Pat. No. 5,836,970 (Pandit) discloses a composite powder of maltodextrin/chitosan salt alginate with some collagen that provides an absorption capacity for wound healing applications.

U.S. Pat. No. 4,952,618 (Olsen) discloses a hydrocolloid adhesive composition for use as a wound dressing having polycationic and polyanionic hydrocolloid particles made of chitosan salt used to provide an increased integrity of the hydrocolloid particle without a decrease of absorbency.

In U.S. Pat. No. 5,196,185 (Silver et al), the inventor discusses that the use of wound dressings comprised of Type I collagen have had limited commercial success because of the difficulty of the physical form of the dressing. Collagen in the particulate form adheres well to wounds because of its high surface areas but is difficult to apply as dry powder because of its high surface charge.

The properties of collagen flakes that are important in wound care applications include absorbency, porosity, density and color (for cosmetic purposes). These properties are important as the dressings are designed to maintain a moist wound environment. For highly exudative wounds, a high absorbency is desired. For wounds with minimal or moderate exudate, it is important that the product not have high absorption abilities to ensure a moist environment.

There are methods available for the production of collagen flakes in prior art literature. The relevance of absorbency also suggests that it is an important implication for the ability of different products to cope with fluid production. None of the prior art literature provides a method for controlling and adjusting the absorbency and porosity of collagen flakes to suit the needs of the user in wound healing. Therefore, a need exists for a method for controlling the properties of collagen flakes, powder, and particles in wound healing applications.

SUMMARY OF THE INVENTION

The present invention provides an absorbent wound dressing that will maintain a moist environment at the wound interface and provide a barrier to microorganisms. The dressing should also provide conformability to the wound surface, vapor/gas permeability, be non-adherent and easily removed without causing additional trauma. The collagen powder (which forms a gel as it absorbs exudate) creates a moist environment that when combined with a secondary covering forms an occlusive dressing over the wound site for the treatment of stage II to IV wounds.

The present invention also provides a method for controlling the absorbency of the collagen powder product.

The present invention further provides a method for controlling the density of the collagen powder product.

The present invention further provides a method for controlling the porosity of the collagen powder product.

The present invention further provides a method for controlling the color of the collagen powder product.

The present invention further provides a wound dressing that uses collagen as its starting material.

The present invention also provides for a collagen powder material that is biocompatible.

DETAILED DESCRIPTION OF THE INVENTION

The present invention provides for a collagen material that can be used as a collagen powder wherein the improvement of the collagen powder is in terms of its porosity, absorbency, density and color.

The terms "flakes," "particles," and "powders" have been loosely defined and used in various literature to indicate a wound product that is in the form of a finely divided solid usually less than 2 mm in dimension.

THE COLLAGEN

Natural insoluble collagen, as defined in U.S. Pat. No. 4,925,924 (Silver et al), and incorporated by reference herein, refers to collagen that cannot be dissolved in an aqueous acidic or alkaline or in any inorganic salt solution without chemical modification and includes hides, splits, and other mammalian or reptilian coverings.

More particularly, natural insoluble collagen refers to the corium, which is the intermediate layer of a bovine hide between the grain and the flesh sides. Collagen constitutes the connective tissue and is the major type of fibrous protein in higher vertebrae. Collagen in its natural state exists in a triple chain helix along with constant periodicity between aligned triple chains. Collagen stimulates angiogenesis, fibroporesis and epidermal growth. The starting material for the present invention is a collagen suspension derived from any of the above sources.

The process of manufacturing collagen products as referred in U.S. Pat. No. 4,925,924, and thus incorporated by reference therein, discloses using collagen as the starting material. It also discloses dispersing an inorganic acid such as hydrochloric acid into a collagen suspension. The collagen suspension has a concentration of about 0.5 to about 1% weight volume. The temperatures at which dispersions are freeze-dried at a product temperature range from about −20° C. to about −35° C., preferably at about −30° C. The dispersing or blending is performed with any suitable mechanical blending means.

The collagen dispersion is deaerated under appropriate vacuum, which has a pressure of less than 0.4 millitorr. The collagen dispersion is then frozen under optimum conditions to obtain a fibrous structure containing numerous pores. When it is desired to have a crosslinked product, the crosslinking can be performed by any method known in the art. The crosslinking as described in U.S. Pat. No. 4,925,924 results in a crosslinked sponge product with stable pores and channels, having dual porosity.

In alternate prior art methods, collagen suspensions may have concentrations of up to 7% weight volume. These suspensions are frozen in trays and freeze-dried at product temperature ranges of about −40° C. to about −10° C. Freeze-drying, like all drying processes, is a method to separate liquid water from a wet solid product, or from a solution or dispersion of given concentration. The main difference is that the liquid water is separated by solidification (i.e. the formation of ice crystals) and subsequent vacuum sublimation instead of evaporation. This allows drying at subzero temperatures which can be advantageous in the case of heat sensitive-products. Collagen flakes are produced when the collagen sponges obtained after freeze-drying, are ground to a suitable size.

Any of the size reduction processes and equipment such as shredders, rotary cutters and dicers, peripheral speed mills and fluid energy superline mills may be used. The process of obtaining collagen flakes as described above is known. The collagen flakes thus obtained are usually white in color, have a high absorbency (of 20 to 40 times), high porosity and light density.

The present invention is illustrated by the following examples contained in the detailed preferred embodiments of the invention. The present disclosure is exemplary of the principles of the invention and is not intended to limit the invention to the embodiments illustrated and described.

In the preferred embodiment, the properties of collagen flakes thus obtained, using prior art methods disclosed above, are improved using the process described below. The properties of collagen flakes are modified by subjecting the flakes to temperatures exceeding 80° C. over varying durations of time. In the preferred embodiment, the freeze-dried collagen flakes are spread over a tray in a compartment type dryer. The flakes may be spread over a tier of trays. Heating is performed by direct contact with a gas such as hydrogen, at a higher temperature, which may be directed parallel or perpendicular to the tray.

In another embodiment of the present invention, the collagen flakes may be heated indirectly by the use of heated shelves, radiation coils or refractory walls inside the housing. The temperature to which the collagen flakes are heated may vary with the length of time used to achieve the desired results.

Generally, lesser amounts of time are required for higher temperatures, to achieve similar results. For instance, collagen flakes which are subjected to a temperature of 140° C. for 180 minutes contained physical properties similar to collagen flakes subjected to 150° C. for 120 minutes. The properties of collagen flakes subjected to those operating conditions were found to be significantly different from the properties of starting collagen flakes. For example, collagen flakes subjected to a temperature of 180° C. over 72 hours exhibited a decrease in both absorbency and porosity.

In yet another embodiment of the present invention, there is a described process of controlling the properties of collagen flakes, which includes heating freeze-dried collagen sponges to varying temperatures at various periods of time prior to size reduction.

EXAMPLE 1

A 4% weight volume collagen suspension was evenly spread on a tray and frozen to a temperature of −20° C. The frozen product was subsequently freeze-dried at a product temperature of −20° C. After freeze-drying, the collagen material was placed in a conventional oven at a temperature of 150° C. for two hours. The collagen material was then reduced into a plurality of particles, and the particles were compared to those obtained from collagen material that had not been heated. It was found that the absorption of collagen flakes was reduced by 25%, and the color had changed from a whitish color to a darkish brown color. The porosity of the flakes decreased by 25%, while the density of the flakes increased by 25%.

EXAMPLE 2

The collagen material obtained in example 1 was subjected to a temperature of 140° C. for 3 hours. The flakes from this collagen material were compared to flakes from untreated collagen material. It was found that the heated collagen flakes were 33% less absorptive, 30% less porous and 30% more dense. The color of the collagen flakes had changed from white to brown.

EXAMPLE 3

Table 1 shows a summary of collagen material from example 1 which were subjected to different conditions, with resultant changes in absorption and porosity.

TABLE 1

| Sample Prototype | Heating Temperature (° C.) | Heating Time (minutes) | % Decrease in Absorption | Porosity |
|---|---|---|---|---|
| Prototype #1 | 140 | 60 | 11.4 | 84% |
| Prototype #2 | 140 | 120 | 21.1 | 75% |
| Pototype #3 | 140 | 180 | 23.5 | 72% |
| Pototype #4 | 150 | 60 | 13.3 | 82% |
| Prototype #5 | 150 | 120 | 25.3 | 71% |
| Prototype #6 | 160 | 60 | 31.3 | 65% |
| Prototype #7 | 180 | 45 | 53.0 | 45% |

1. Table 1 shows the percent of decrease in absorption increases as the heating time or temperature is increased, and the porosity decreases as the heating time and temperature are increased. Thus, it has been discovered that the absorbency and porosity of collagen material will controllably decrease as at least one of time and temperature are controllably increased. This enables the manufacture to selectively control the absorption and porosity of an absorbent wound dressing. The selected collagen powder forms a gel as it absorbs exudate, and creates a moist environment, which combined with a secondary covering forms an occlusive dressing over the wound site for selective treatment of stage II to stage IV wounds.

METHODS OF MEASUREMENT

Measurement of Absorption:

1.5 to 1.8 grams of collagen flakes were sealed in a moisture permeable pouch and soaked in a solution containing distilled water, or saline solution, for 1.5 hours. The pouches were then removed, allowed to dry, and blotted to remove excess fluids. The net gain of the collagen flakes was then determined. Absorption was determined by calculating the net gain in weight of collagen flakes divided by the initial weight of collagen flakes.

Measurement of Density:

The weight of 10 cc of particles was determined. The density was then measured by dividing the weight of particles (in grams) by the volume (cc.) and expressed in g/cc.

Measurement of Porosity:

A porosity of 0% was assumed for a density of 1 g/cc and of 100% for a density of 0 g/cc. Intermediate percentages of porosity were determined by determining a linear relationship.

Measurement of Color:

A standard color system (Pantone) was used to compare colors of different products after being subjected to different conditions.

The results of varying temperature and time on the porosity of collagen is clearly shown in FIG. 1. These results are not shown, nor made obvious by the cited prior art. Thus, the porosity of collagen may be easily varied to suit the specific conditions of a wound, in accordance with the disclosure provided.

The invention being thus described, it will be evident that this invention may be varied in many ways, and such adaptations and variations are intended to be included within the scope of this invention, and the following claims.

| | | |
|---|---|---|
| 4925924 | Silver et al | 530/356 |
| 5836970 | Pandit | 606/213 |
| 4952618 | Olsen | 524/17 |
| 5196185 | Silver et al | 424/45 |
| 6136341 | Petito | 424/446 |
| 5869080 | McGregor et al | 424/426 |
| 6177609 | Castroetal | 623/11 |
| 6025327 | Alkayali | 514/2 |

OTHER REFERENCES

1. Cost-Effective Pressure Ulcer Management in Extended Care; Ostomy/Wound Management Vol. 41 No. 7A August 1995
2. When to Use Hydrocolloid Dressing; Advances in Skin Care & Wound Care—The Journal for Prevention & Healing
3. A Structured Approach to the Selection of Dressings—The Electronic Journal of Wound Management Practice—World Wide Wounds
4. Common Wound Dressing Categories—www.ruralfamilymedicine.org
5. A Comparative Study of the Properties of the Twelve Hydrocolloid Dressings—The Electronic Journal of Wound Management Practice
6. Guidance on Dressing Selection—www.smtl.co.uk
7. Hydrocolloid Dressings—Wound Expert—www.medicaledu.com
8. Food Processing and Preservation—www.encarta.msn.com

I claim:

1. A process of controlling the absorbency of a collagen material, comprising the steps of:
    a) converting the collagen material into collagen particles;
    b) dispersing the collagen particles into an aqueous solution;
    c) freezing the collagen particles; and
    d) freeze-drying said collagen particles at a predetermined temperature selected to be between −20° C. and −35° C., and subsequently
    e) heating said collagen particles to a predetermined temperature range selected to be between 80° C. and 200° C. for a predetermined length or time; and
    f) reducing the size of the collagen particles whereby the absorbency and the porosity of the collagen material may be reduced.

2. A process of controlling the absorbency or a collagen material, according to claim 1, wherein the collagen material used is a natural collagen derived from at least one of mammalian and reptilian coverings, which exist in a triple chain helix having constant periodicity between aligned triple chains.

3. A process of controlling the absorbency of a collagen material, according to claim 1, wherein the heating of the collagen material is accomplished using at least one of: a conventional oven, heating shelves, refractory walls, hot gas, and radiation coils.

4. A process of controlling the absorbency of a collagen material, according to claim 1, wherein said collagen particles are heated to a predetermined temperature range between 80° C. and 200° C., for a predetermined length of time, and said heating is done prior to size reduction of the collagen powder particles.

5. A process of controlling the absorbency of a collagen material, according to claim 4, wherein the size reduction of the collagen particles is done using at least one of: a rotary cutter, a shredder, a dicer, a mill, and a grinder.

6. A process of controlling the absorbency of a collagen material, according to claim 1, wherein the absorption of the said collagen material is selected to be between 2 and 20 times the weight of the collagen material.

7. A process of controlling the absorbency of a collagen material, according to claim 1, wherein the density of the said collagen material is selected to be between 0.1 g/cc and 1.0 g/cc.

8. A process of controlling the absorbency of a collagen material, according to claim 1, wherein the collagen particles are reduced to a powder, and used as an absorbent wound dressing that provides a non-adherency barrier, in combination with a vapor/gas permeability, and a conformability to the wound surface.

9. A process of controlling the absorbency of a collagen material, according to claim 1, wherein the color of the collagen particles ranges from white cream to dark brown, and said color of the collagen particles selectively darken with a controlled increase in at least one of time and temperature.

10. A process of controlling the absorbency of a collagen material, according to claim 1, wherein the collagen particles are converted into a powder, with the porosity, absorbency, density and color of the collagen powder selectively dependent upon the time and temperature used to prepare the collagen particles prior to reducing the collagen particles into a powder.

11. The process of controlling the absorbency of a collagen material, according to claim 10, wherein the collagen powder forms a gel as it absorbs exudates, and creates a moist environment, which combined with a secondary covering forms an occlusive dressing over the wound site for selective treatment of stage II to stage IV wounds.

12. A process of controlling the absorbency of a collagen material, comprising the steps of:
   a) changing the collagen material into collagen flakes;
   b) dispersing said collagen flakes into an aqueous solution;
   c) freezing said collagen flakes trays; and
   d) freeze-drying said collagen flakes at a pre-determined temperature selected to be between −20° C. and −35° C.; and subsequently heating said collagen flakes to a predetermined temperature range selected to be between 80° C. and 200° C. for a predetermined length of time; whereby the absorbency of said collagen flakes will controllably decrease as at least one of said time and temperature is controllably increased; and
   e) reducing the heated collagen flakes into a powder, with the porosity, absorbency, density and color of the collagen powder selectively dependent upon the said time and temperature used to heat the collagen material prior to reducing the collagen flakes into a powder.

13. A process of controlling the absorbency of a collagen material, according to claim 12, wherein the collagen material used is a natural collagen derived from at least one of mammalian and reptilian coverings, which exist in a triple chain helix having constant periodicity between aligned triple chains.

14. A process of controlling the absorbency of a collagen material, according to claim 12, wherein the heating of the collagen is accomplished using at least one of: a conventional oven, heating shelves, refractory wall, hot gas, and radiation coils.

15. A process of controlling the absorbency of a collagen material, according to claim 12, wherein said collagen material is heated to a predetermined temperature range between 80° C. and 200° C., for a predetermined length of time, and said heating is done prior to size reduction of the collagen flakes into a powder.

16. A process of controlling the absorbency of a collagen material, according to claim 12, wherein the absorption of the said collagen material is selected to be between 2 to 20 times the weight of the collagen material.

17. A process of controlling the absorbency of a collagen material, according to claim 12, wherein the density of the said collagen material is selected to be between 0.1 g/cc and 1.0 g/cc.

18. A process of controlling the absorbency of a collagen material, according to claim 12, wherein the collagen powder is used as an absorbent wound dressing that provides a non-adherency barrier, with a vapor/gas permeability and a conformability to the wound surface.

19. A process of controlling the absorbency of a collagen material, according to claim 12, wherein the color of said collagen flakes ranges from white cream to dark brown, and said color of said collagen flakes selectively darkens with an increase in at least one of time and temperature during the heating process.

20. A process of controlling the absorbency of a collagen material according to claim 12, wherein the collagen powder forms a gel as it absorbs exudates, and creates a moist environment, which combined with a secondary covering forms an occlusive dressing over the wound site for selective treatment of stage II to stage IV wounds.

21. A process or controlling the absorbency of a collagen material, comprising the steps of:
   a) converting the collagen material into collagen flakes;
   b) dispersing the said collagen flakes into an aqueous solution;
   c) freezing said collagen flakes; and
   d) freeze-drying said collagen flakes at a predetermined temperature selected to be between −20° C. and −35° C.; and subsequently heating said collagen flakes to a predetermined temperature range selected to be between 80° C. and 200° C. for a predetermined length of time; whereby the absorbency of said collagen flakes will controllably decrease as at least one of said time and temperature is controllably increased; and
   e) converting the heated collagen flakes into a powder, with the porosity, absorbency, density and color of the collagen powder selectively dependent upon the time and temperature used to heat the collagen flakes prior to grinding the collagen flakes into a powder;
   f) the density of said collage powder being selected to be between 0.1 g/cc to 1.0 g/cc;
   g) the absorption of said collage powder being selected to be between 2 to 20 times the weight of the product; and
   h) said collage powder is forming a gel as it absorbs exudates, and creates a moist environment, which combined with a secondary covering forms an occlusive dressing over the wound site for selective treatment of stage II to stage IV wounds.

22. The process of claim 1 wherein said collagen flakes arc white in color.

23. The process of claim 12 wherein said collagen powder is white in color.

24. The process of claim 21 wherein said collagen powder is white in color.

* * * * *